United States Patent [19]

Johnson

[11] Patent Number: 4,528,183

[45] Date of Patent: Jul. 9, 1985

[54] COMPOSITION FOR USE WITH INDOOR TANNING EQUIPMENT

[76] Inventor: Geoffrey W. A. Johnson, 19230 Southeast 48th Pl., Issaquah, Wash. 98027

[21] Appl. No.: 488,588

[22] Filed: Apr. 25, 1983

[51] Int. Cl.³ .................. A61K 7/42; A61K 35/78; A61K 31/355; A61K 47/00
[52] U.S. Cl. ........................... 424/59; 424/78; 424/195.1; 514/458; 514/782
[58] Field of Search .............. 424/59, 60, 195, 358, 424/78, 284

[56] References Cited

U.S. PATENT DOCUMENTS 4,002,733  1/1977  Degen et al. .................. 424/59
4,070,450  1/1978  Barner et al. ................. 424/59
4,154,823  5/1979  Schutt .......................... 424/195
4,335,103  6/1982  Barker et al. ................. 424/59

FOREIGN PATENT DOCUMENTS 1959602  6/1970  Fed. Rep. of Germany ........ 424/59

Primary Examiner—Sidney Marantz
Assistant Examiner—Shawn P. Foley
Attorney, Agent, or Firm—Seed and Berry

[57] ABSTRACT

A non-greasy, water-based skin preparation composition is disclosed for application to the skin prior to exposure of the skin to ultraviolet rays of indoor tanning equipment. The composition consists essentially of a major amount of water, a water-soluble, high molecular weight resin, a neutralizing agent for the resin, and minor amounts of banana oil, aloe vera juice, and Vitamin E.

2 Claims, No Drawings

COMPOSITION FOR USE WITH INDOOR TANNING EQUIPMENT

DESCRIPTION

TECHNICAL FIELD

The present invention relates to a non-greasy, non-sticky skin preparation composition for application to the skin prior to exposure to the ultraviolet rays of indoor tanning equipment.

BACKGROUND ART

Indoor tanning equipment employs banks of ultraviolet lights positioned beneath and above a planar surface which is transparent to ultraviolet radiation have become increasingly popular for acquiring a tan. Generally, such tanning equipment employs a planar surface made out of a material transparent to ultraviolet radiation, such as Plexiglas. The source of ultraviolet radiation is positioned above and below the UVT Plexiglas on which the person lies.

Tanning lotions prepared for outdoor use cannot be used for such tanning equipment because the lotions tend to smear on the UVT Plexiglas and reduce the amount of ultraviolet radiation which gets to the skin. Manufacturers of such tanning equipment specifically prohibit use of outdoor tanning lotions.

DISCLOSURE OF INVENTION

A non-sticky, non-greasy, water-based skin preparation composition is disclosed for application to the skin prior to exposure to the ultraviolet rays of indoor tanning equipment. The composition consists essentially of a major amount of water, sufficient amounts of a water-soluble, high molecular weight resin, a sufficient amount of a neutralizing agent for neutralization of the resin, small amounts of banana oil, aloe vera juice, and Vitamin E (dl-α-tocopherols).

BEST MODE FOR CARRYING OUT INVENTION

Indoor tanning equipment generally uses an ultraviolet transparent surface, such as UVT Plexiglas, on which the person lies, with banks of ultraviolet lights positioned beneath and above the planar surface. It is essential for use in indoor tanning equipment that the composition spread on the skin be one which is not greasy and which does not contaminate the surface of the equipment to passage of ultraviolet radiation of the wavelength needed for effective tanning. It is also essential that the composition have a consistency for each and uniform application to the skin.

The composition of this invention consists essentially of from 2%–5% by weight of a high molecular weight, water-soluble resin which is non-toxic, 1%–3% by weight of a neutralizing agent for the resin, 0.05%–1.% by weight, respectively, of a fragrance, such as banana oil, aloe vera juice, and Vitamin E (dl-α-tocopherols). The remaining 90–96% by weight of the composition is water. The resulting composition is non-greasy, non-toxic, and useful with indoor tanning equipment. The compositions are prepared by sprinkling the high molecular weight resin in powder form into the vortex of a vigorously agitated amount of water, adding the neutralizing agent to form a gel of the water solution, and then adding the amounts of aloe vera and banana oil, previously mixed with the Vitamin E. The preferred composition is:

|  | % by weight |
| --- | --- |
| Water | 92 |
| Carbomer (Carbopol 934 or 940) | 4 |
| Triethanolamine | 2 |
| Banana Oil | 0.75 |
| Aloe Vera Juice | 0.75 |
| Vitamin E (dl-α-tocopherols) | 0.5 |

The preferred resins used are high molecular weight carboxy vinyl polymers which are commercially available as a dry powder in acid form and which generally require neutralization to develop optimum properties. The preferred resins are sold under the trademark CARBOPOL by B. F. Goodrich.

A small amount of color can be added to the composition if desired. The compositions have excellent shelf stability and can be safely used as desired with indoor tanning equipment.

What is claimed is:

1. A non-greasy, non-toxic, water based skin preparation composition for application to the skin prior to exposure of the skin to the ultraviolet rays of indoor tanning equipment, consisting essentially of:
   90–96% by weight water;
   2–5% by weight of a high molecular weight carboxy vinyl resin;
   1–3% by weight triethanolamine as a neutralizing agent for the resin; and
   the remainder banana oil, aloe vera juice and vitamin E (dl-α-tocopherols).

2. A method of preparing the skin for exposure to ultraviolet radiation from the ultraviolet rays of indoor tanning equipment, comprising:
   applying to the skin a skin preparation composition consisting essentially of:
   90–96% by weight water;
   2–5% by weight of a high molecular weight carboxy vinyl resin;
   1–3% by weight triethanolamine as a neutralizing agent for the resin;
   the remainder banana oil, aloe vera juice and vitamin E (dl-α-tocopherols); and
   exposing the skin with the applied composition to ultraviolet radiation from indoor tanning equipment.

* * * * *